US00PP20819P2

(12) United States Plant Patent
Dekker

(10) Patent No.: US PP20,819 P2
(45) Date of Patent: Mar. 9, 2010

(54) ***CHRYSANTHEMUM* PLANT NAMED 'DEKGOMBA GREEN'**

(50) Latin Name: *Chrysanthemum×morifolium*
Varietal Denomination: Dekgomba Green

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 0 days.

(21) Appl. No.: 12/284,878

(22) Filed: Sep. 22, 2008

(51) Int. Cl.
*A01H 5/00* (2006.01)

(52) U.S. Cl. ..... Plt./286

(58) Field of Classification Search ..... Plt./286
See application file for complete search history.

(56) References Cited

U.S. PATENT DOCUMENTS

PP17,815 P2 * 6/2007 Dekker ..... Plt./294
PP19,352 P2 * 10/2008 Dekker ..... Plt./286

OTHER PUBLICATIONS

UPOV ROM GTITM Computer Database, GTI Jouve Retrieval Software 2008/03 Citation for 'Dekgomba Green'.*

* cited by examiner

*Primary Examiner*—Wendy C. Haas
(74) *Attorney, Agent, or Firm*—C. A. Whealy

(57) ABSTRACT

A new and distinct cultivar of *Chrysanthemum* plant named 'Dekgomba Green', characterized by its single-type inflorescences with green yellow-colored ray florets; strong and upright flowering stems; freely flowering habit; early and uniform flowering response; and good postproduction longevity.

2 Drawing Sheets

Botanical designation: *Chrysanthemum×morifolium.*
Cultivar denomination: 'Dekgomba Green'.

BACKGROUND OF THE INVENTION

The present invention relates to a new and distinct cultivar of *Chrysanthemum* plant, botanically known as *Chrysanthemum×morifolium*, commercially grown as a cut flower and hereinafter referred to by the name 'Dekgomba Green'.

The new *Chrysanthemum* is a product of a planned breeding program conducted by the Inventor in Hensbroek, The Netherlands. The objective of the breeding program is to create new freely flowering single-type *Chrysanthemum* cultivars with unique ray floret coloration and excellent postproduction longevity.

The new *Chrysanthemum* originated from a cross-pollination made by the Inventor in Hensbroek, The Netherlands in February, 2006 of a proprietary selection of *Chrysanthemum×morifolium* identified as code No. 03.7355.04, not patented, as the female, or seed, parent with a proprietary selection of *Chrysanthemum×morifolium* identified as code No. 03.7938.02, not patented. The new *Chrysanthemum* was discovered and selected by the Inventor as a flowering plant from within the progeny of the stated cross-pollination in a controlled greenhouse environment in Hensbroek, The Netherlands in November, 2006.

Asexual reproduction of the new *Chrysanthemum* by terminal cuttings in a controlled greenhouse environment in Hensbroek, The Netherlands since December, 2006, has shown that the unique features of this new *Chrysanthemum* are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dekgomba Green'. These characteristics in combination distinguish 'Dekgomba Green' as a new and distinct cultivar of *Chrysanthemum:*

1. Single-type inflorescences with green yellow-colored ray florets.
2. Strong and upright flowering stems.
3. Freely flowering habit.
4. Early and uniform flowering response; plants flower about 44 days after the start of photoinductive treatments.
5. Good postproduction longevity; plants maintain good substance for about three weeks in an interior environment.

Plants of the new *Chrysanthemum* differ from plants of the female parent selection in the following characteristics:

1. Plants of the new *Chrysanthemum* are more vigorous than plants of the female parent selection.
2. Plants of the new *Chrysanthemum* have larger inflorescences than plants of the female parent selection.
3. Ray florets of plants of the new *Chrysanthemum* are yellow green in color whereas ray florets of plants of the female parent selection are white in color.

Plants of the new *Chrysanthemum* differ from plants of the male parent selection in the following characteristics:

1. Plants of the new *Chrysanthemum* are not as vigorous as plants of the male parent selection.
2. Plants of the new *Chrysanthemum* have smaller inflorescences than plants of the male parent selection.
3. Ray florets of plants of the new *Chrysanthemum* are yellow green in color whereas ray florets of plants of the male parent selection are white in color.

Plants of the new *Chrysanthemum* can be compared to plants of *Chrysanthemum×morifolium* 'Deklindi White', disclosed in U.S. Plant Pat. No. 17,815. In side-by-side comparisons conducted in Hensbroek, The Netherlands, plants of the new *Chrysanthemum* differed from plants of 'Deklindi White' in the following characteristics:

1. Plants of the new *Chrysanthemum* were more vigorous than plants of 'Deklindi White'.
2. Plants of the new *Chrysanthemum* flowered three days later than plants of 'Deklindi White'.
3. Plants of the new *Chrysanthemum* had larger inflorescences than plants of 'Deklindi White'.
4. Plants of the new *Chrysanthemum* and 'Deklindi White' differed in ray floret color as plants of 'Deklindi White' had white-colored ray florets.

BRIEF DESCRIPTION OF THE PHOTOGRAPHS

The accompanying colored photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering stem of 'Dekgomba Green' grown as a spray type.

The photograph on the second sheet comprises close-up views of the upper (top of photograph) and lower surfaces (bottom of photograph) of typical inflorescences and leaves of 'Dekgomba Green'.

DETAILED BOTANICAL DESCRIPTION

The aforementioned photographs and following observations and measurements describe plants grown during the summer in Hensbroek, The Netherlands, under commercial practice in a glass-covered greenhouse. Plants were initially given two weeks of long day/short night treatments followed by short day/long night treatments to induce flower initiation and development. During the production of the plants, day temperatures ranged from 18° C. to 25° C., night temperatures ranged from 20° C. to 22° C. and light levels were about 7 kilolux. Plants were pinched one time and were eight weeks from planting when the photographs and the description were taken. In the following description, color references are made to The Royal Horticultural Society Colour Chart, 2001 Edition, except where general terms of ordinary dictionary significance are used.

Botanical classification: *Chrysanthemum×morifolium* 'Dekgomba Green'.

Parentage:

*Female, or seed, parent.*—Proprietary selection of *Chrysanthemum×morifolium* identified as code No. 03.7355.04, not patented.

*Male, or pollen, parent.*—Proprietary selection of *Chrysanthemum×morifolium* identified as code No. 03.7938.02, not patented.

Propagation:

*Type.*—Terminal vegetative cuttings.

*Time to initiate roots, summer.*—About four days at 20° C.

*Time to initiate roots, winter.*—About six days at 20° C.

*Time to produce a rooted young plant, summer.*—About 13 days at 20° C.

*Time to produce a rooted young plant, winter.*—About 15 days at 20° C.

*Root description.*—Fine, fibrous; light brown in color.

*Rooting habit.*—Freely branching, moderately dense.

Plant description:

*Appearance/growth habit.*—Herbaceous single-type cut flower that is typically grown as a spray-type. Moderately vigorous growth habit.

*Flowering stem description.*—Aspect: Erect. Length: About 60 cm. Spray diameter: About 14 cm to 16 cm. Diameter: About 6 mm. Lateral branch length: About 20 cm to 25 cm. Internode length: About 1.5 cm. Texture: Finely pubescent; longitudinally ridged. Color: Close to 144B.

*Foliage description.*—Arrangement: Alternate; simple. Length: About 3 cm to 8 cm. Width: About 1.5 cm to 4 cm. Apex: Cuspidate. Base: Attenuate. Margin: Palmately lobed; sinuses divergent. Texture, upper and lower surfaces: Pubescent, slightly rough; veins prominent on lower surface. Venation pattern: Pinnate, reticulate. Color: Developing leaves, upper surface: Close to 137C. Developing leaves, lower surface: More green than 147B. Fully developed leaves, upper surface: Close to 137B; venation, lighter than 148B. Fully developed leaves, lower surface: Close to 147B; venation, close to 147C. Petiole: Length: About 5 mm to 7 mm. Diameter: About 3 mm. Texture, upper and lower surfaces: Slightly rough. Color, upper surface: Close to 147C. Color, lower surface: Close to 146D.

Inflorescence description:

*Appearance.*—Single-type inflorescence form with oblong-shaped ray florets. Inflorescences borne on terminals, arising from leaf axils. Ray and disc florets develop acropetally on a capitulum. Inflorescences moderately fragrant.

*Flowering response.*—Under natural conditions, plant flower in the autumn/winter in the Northern Hemisphere. At other times of the year, inflorescence initiation and development can be induced under short day/long night conditions (at least 13.5 hours of darkness). Early and uniform flowering response; plants exposed to eight days of long day/short night conditions after planting followed by photoinductive short day/long night conditions flower about 44 days later when grown as a spray-type.

*Postproduction longevity.*—In an interior environment, inflorescences and foliage will maintain good color and substance for about three weeks; inflorescences persistent.

*Quantity of inflorescences.*—Freely flowering habit; when grown as a spray type, about 60 inflorescences per flowering stem develop.

*Inflorescence size.*—Diameter: About 2 cm. Depth (height): About 5 mm to 8 mm. Disc diameter: About 1 cm. Receptacle height: About 3 mm to 4 mm. Receptacle diameter: About 4 mm. Receptacle color: Close to 145B.

*Inflorescence buds.*—Shape: Flattened spherical to rounded. Height: About 3 mm to 4 mm. Diameter: About 5 mm to 8 mm. Color: Between 144B and 145C.

*Ray florets.*—Length: About 1 cm to 1.2 cm. Width: About 3 mm to 5 mm. Shape: Oblong. Apex: Rounded. Base: Attenuate. Margin: Entire. Angle:

Initially upright to close to about 30° from vertical; eventually reflexing. Texture, upper and lower surfaces: Smooth, glabrous; satiny. Number per inflorescence: About 35 arranged in about two to three whorls. Color: When opening, upper surface: Close to 150B to 150C. When opening, lower surface: Close to 150A to 150B. Fully opened, upper surface: Close to 154D; with development, color becoming closer to 150D. Fully opened, lower surface: Close to 150C; with development, color becoming closer to 154D.

*Disc florets.*—Shape: Fused tubular, elongated. Apex: Dentate. Length: About 4 mm to 5 mm. Diameter: About 1 mm. Number per inflorescence: About 180, massed at the center. Color, immature: Apex: Close to 144C. Mid-section: Close to 6A. Base: Close to 145C. Color, mature: Apex: Close to 154C. Mid-section: Close to 12A. Base: Close to 145C.

*Involucral bracts.*—Length: About 4 mm to 8 mm. Width: About 2 mm to 4 mm. Shape: Oblong. Apex: Obtuse. Base: Obtuse to truncate. Margin: Entire. Texture, upper and lower surfaces: Smooth, glabrous. Number per inflorescence: About 20 arranged in about two to three whorls. Color, upper surface: Close to 146B. Color, lower surface: Close to 144A.

*Peduncles.*—Length: About 6 cm to 8 cm. Diameter: About 1.5 mm. Angle: Erect to about 30° from vertical. Strength: Moderately strong. Texture: Slightly pubescent; longitudinally ridged. Color: Close to 146B.

*Reproductive organs.*—Androecium: Not observed. Gynoecium: Present on both ray and disc florets. Style length: About 4 mm. Style color: Close to 145D. Stigma color: Close to 154A.

*Seed/fruit.*—Seed and fruit production has not been observed.

Disease/pest resistance: Resistance to pathogens and pests common to *Chrysanthemums* has not been observed on plants grown under commercial conditions.

It is claimed:

1. A new and distinct *Chrysanthemum* plant named 'Dekgomba Green' as illustrated and described.

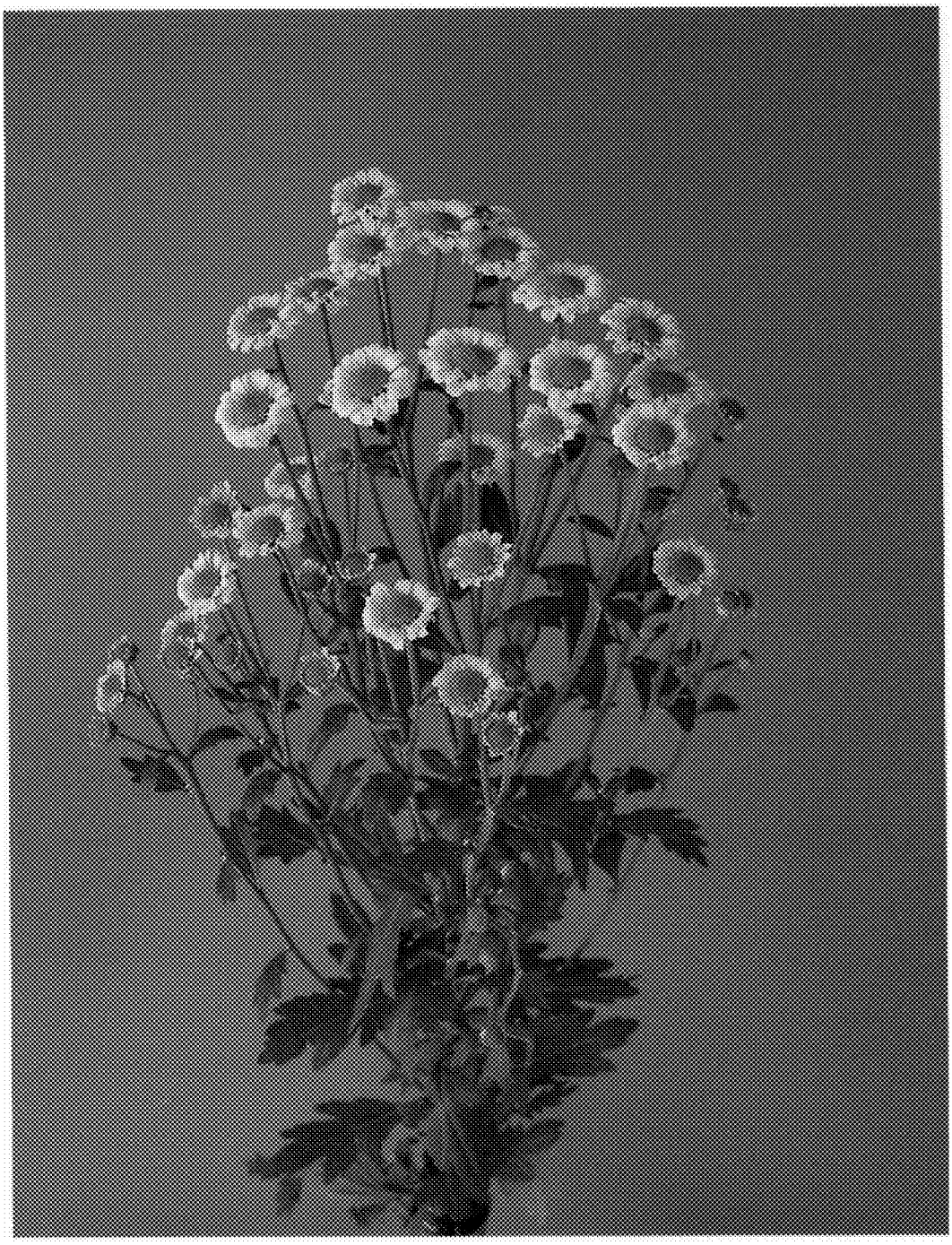

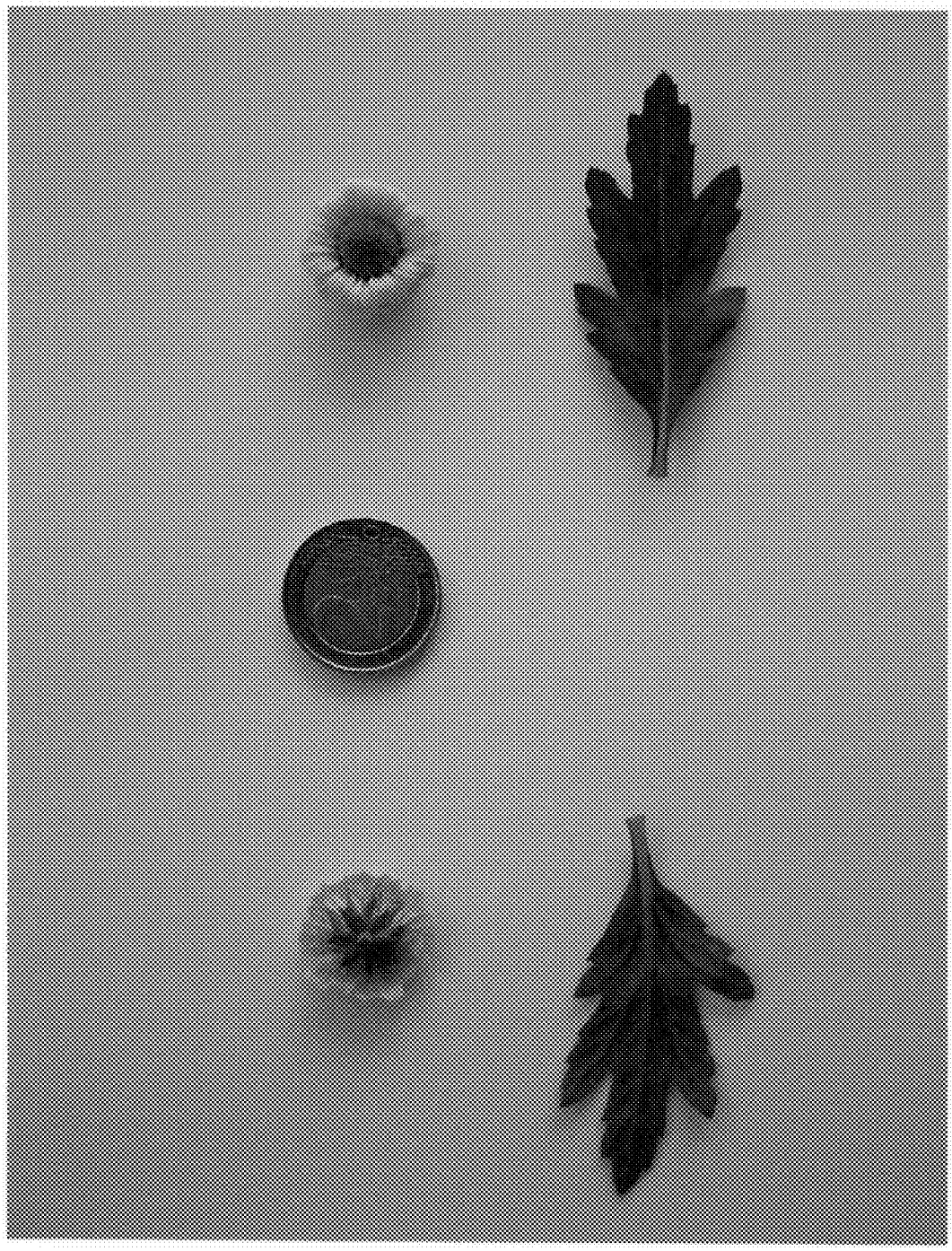

* * * * *